United States Patent
Margallo Balbás

(10) Patent No.: US 12,239,363 B2
(45) Date of Patent: Mar. 4, 2025

(54) ABLATION CATHETER WITH A PATTERNED TEXTURED ACTIVE AREA

(71) Applicant: MEDLUMICS S.L., Madrid (ES)

(72) Inventor: Eduardo Margallo Balbás, Madrid (ES)

(73) Assignee: Medlumics S.L., Madrid (ES)

(*) Notice: Subject to any disclaimer, the term of this patent is extended or adjusted under 35 U.S.C. 154(b) by 0 days.

(21) Appl. No.: 16/210,735

(22) Filed: Dec. 5, 2018

(65) Prior Publication Data

US 2019/0192220 A1    Jun. 27, 2019

Related U.S. Application Data

(60) Provisional application No. 62/610,760, filed on Dec. 27, 2017.

(51) Int. Cl.
*A61B 18/02* (2006.01)
*A61B 18/12* (2006.01)
(Continued)

(52) U.S. Cl.
CPC .......... *A61B 18/1492* (2013.01); *A61B 18/02* (2013.01); *A61B 18/12* (2013.01);
(Continued)

(58) Field of Classification Search
CPC ..... A61B 18/1492; A61B 18/02; A61B 18/12; A61B 18/24; A61B 2034/301;
(Continued)

(56) References Cited

U.S. PATENT DOCUMENTS 5,281,213 A * 1/1994 Milder ............... A61B 18/1492
607/105
2001/0031942 A1    10/2001 Tollner et al.
(Continued)

FOREIGN PATENT DOCUMENTS

EP    2 796 103 A1    10/2014
EP    3 157 456 B1    3/2018
(Continued)

OTHER PUBLICATIONS

Tsipenyuk, A., et al., "Use of biomimetic hexagonal surface texture in friction against lubricated skin," J. R. Soc. Interface (Mar. 12, 2014), 11 (94), available at: http://dx.doi.org/10.1098/rsif.2014.0113.
(Continued)

*Primary Examiner* — Ankit D Tejani
*Assistant Examiner* — Joshua Brendon Solomon
(74) *Attorney, Agent, or Firm* — Sterne, Kessler, Goldstein & Fox P.L.L.C.

(57) ABSTRACT

Described herein are devices and methods for performing ablation using ablation catheters with one or more patterned and textured active areas. An ablation catheter includes a proximal section, a distal section, and a sheath coupled between the distal section and the proximal section. The distal section includes an active area with a patterned, textured surface that is configured to apply radiofrequency (RF) energy, cryogenic cooling, or laser energy output to a portion of target tissue, such that the portion of target tissue is ablated. The patterned, textured surface of the active area is configured to maintain contact between the target tissue and the active area.

20 Claims, 7 Drawing Sheets

(51) Int. Cl.
*A61B 18/14* (2006.01)
*A61B 18/00* (2006.01)
*A61B 18/24* (2006.01)
*A61B 34/30* (2016.01)

(52) U.S. Cl.
CPC .............. *A61B 2018/00095* (2013.01); *A61B 2018/00125* (2013.01); *A61B 2018/0016* (2013.01); *A61B 2018/00273* (2013.01); *A61B 2018/00351* (2013.01); *A61B 2018/00404* (2013.01); *A61B 2018/00482* (2013.01); *A61B 2018/00488* (2013.01); *A61B 2018/00577* (2013.01); *A61B 2018/00982* (2013.01); *A61B 2018/0212* (2013.01); *A61B 18/24* (2013.01); *A61B 2034/301* (2016.02)

(58) Field of Classification Search
CPC ........... A61B 2018/00095; A61B 2018/00125; A61B 2018/0016; A61B 2018/00273; A61B 2018/00351; A61B 2018/00404; A61B 2018/00482; A61B 2018/00488; A61B 2018/00577; A61B 2018/00982; A61B 2018/0212

See application file for complete search history.

(56) References Cited

U.S. PATENT DOCUMENTS

| | | | |
|---|---|---|---|
| 2002/0198520 A1* | 12/2002 | Coen | A61B 18/1492 606/41 |
| 2003/0208252 A1 | 11/2003 | O'Boyle et al. | |
| 2004/0116922 A1* | 6/2004 | Hovda | A61B 18/148 606/41 |
| 2005/0119653 A1* | 6/2005 | Swanson | A61B 18/1492 606/49 |
| 2005/0146841 A1* | 7/2005 | Schott | H01G 9/042 361/508 |
| 2005/0171524 A1* | 8/2005 | Stern | A61B 18/06 606/41 |
| 2006/0025838 A1* | 2/2006 | Laufer | A61B 18/1482 607/99 |
| 2006/0167448 A1* | 7/2006 | Kozel | A61B 18/1492 606/41 |
| 2008/0089641 A1 | 4/2008 | Feldchtein | |
| 2008/0294158 A1* | 11/2008 | Pappone | A61B 18/1492 606/41 |
| 2009/0018393 A1 | 1/2009 | Dick et al. | |
| 2009/0306520 A1 | 12/2009 | Schmitt et al. | |
| 2010/0041986 A1 | 2/2010 | Nguyen et al. | |
| 2010/0046953 A1 | 2/2010 | Shaw et al. | |
| 2010/0057074 A1* | 3/2010 | Roman | A61B 18/1492 606/33 |
| 2011/0190659 A1* | 8/2011 | Long | A61B 18/1492 600/564 |
| 2011/0270046 A1* | 11/2011 | Paul | A61B 5/065 600/300 |
| 2012/0053645 A1* | 3/2012 | Ayanoor-Vitikkate | A61N 1/36064 607/2 |
| 2012/0265190 A1* | 10/2012 | Curley | A61B 18/1477 606/28 |
| 2014/0052120 A1* | 2/2014 | Benscoter | A61L 29/02 606/41 |
| 2014/0163548 A1* | 6/2014 | Christian | A61B 18/1492 606/41 |
| 2014/0188099 A1* | 7/2014 | Przybyszewski | A61B 18/14 606/33 |
| 2017/0027639 A1* | 2/2017 | Margallo Balb S . | A61B 5/0084 |

FOREIGN PATENT DOCUMENTS

| | | | |
|---|---|---|---|
| WO | WO 2012/068273 A1 | 5/2012 | |
| WO | WO 2017/212334 A1 | 12/2017 | |

OTHER PUBLICATIONS

Dunn, Andrew, "Laser Surface Texturing for High Friction and Other Surface Engineering Applications," Ph.D. Dissertation (Jun. 2016), Heriot-Watt University School of Engineering and Physical Sciences.

Chen, Huawei, et al. "Bioinspired Surface for Surgical Graspers Based on the Strong Wet Friction of Tree Frog Toe Pads," ACS Appl. Mater. & Interfaces (Jun. 8, 2015), pp. 13987-13995, 7 (25), DOI: 10.1021/acsami.5b03039.

International Search Report and Written Opinion of the International Searching Authority directed to International Patent Application No. PCT/EP2018/086319, mailed Apr. 12, 2019; 12 pages.

Fleming, Christine, et al., "Optical Coherence Tomography Imaging of Cardiac Radiofrequency Ablation Lesions, " Poster presented at Biomedical Optics 2008, St. Petersburg, Florida, Mar. 16-19, 2008; 7 pages.

Fleming, Christine, et al., "Real-Time Imaging of Radiofrequency Cardiac Ablation Using Optical Coherence Tomography," Osa Technical Digest (CD) (Optical Society of America, Mar. 2008), paper BMD88, Mar. 2008; 3 pages.

Boppart, Stephen A., et al., "Real-Time Optical Coherence Tomography for Minimally Invasive Imaging of Prostrate Ablation," Computer Aided Surgery 6:94-103, Accepted Feb. 2001, published online Jan. 2010; 10 pages.

Patel, Nirlep A., et al., "Guidance of Aortic Ablation Using Optical Coherence Tomography," The International Journal of Cardiovascular Imaging 19:171-178, Apr. 2003; 8 pages.

De Boer, Johannes F., et al., "Two-Dimensional Birefringence Imaging in Biological Tissue Using Polarization Sensitive Optical Coherence Tomography," Spie vol. 3196, 0277, pp. 32-37, Jan. 1998; 6 p.

Everett, M.J., et al., "Birefringence Characterization of Biological Tissue By Use of Optical Coherence Tomography," Optics Letters, vol. 23, No. 3, Feb. 1, 1998; 3 pages.

Fleming, Christine, "Characterization of Cardiac Tissue Using Optical Coherence Tomography," Department of Biomedical Engineering, Case Western Reserve University, May 2010; 210 pages.

* cited by examiner

ABLATION CATHETER WITH A PATTERNED TEXTURED ACTIVE AREA

CROSS-REFERENCE TO RELATED APPLICATIONS

This application claims the benefit under 35 U.S.C. § 119(e) of U.S. provisional patent application Ser. No. 62/610,760, filed Dec. 27, 2017, which is incorporated by reference herein in its entirety.

BACKGROUND

Field

Embodiments of the invention relate to designs of, and methods of using, an ablation catheter with one or more patterned, textured active areas.

Background

Ablation is a medical technique for producing tissue necrosis. It is used to help treat different pathologies including cancer, Barret's esophagus, or cardiac arrhythmias, among others. For radiofrequency (RF) ablation, the application of alternating current with an oscillating frequency above several hundreds of kHz avoids the stimulation of excitable tissue while delivering heat by means of the Joule's effect. The increase in tissue temperature produces denaturation of the biological molecules, including proteins such as collagen, myosin, or elastin. Traditionally, RF ablation is done by placing an external electrode on the patient's body, and applying an alternating potential to the tip of a catheter that is placed in contact with the tissue to be treated within the patient's body. In some cases, various energy sources may be utilized for ablation, including cryogenic cooling for cryoablation, radiofrequency, microwave, laser, ultrasound, and the like. The ablation effect depends on a number of factors, including applied electrical power, quality of the electrical contact, local tissue properties, presence of blood flow close to the tissue surface, and the effect of irrigation. Because of the variability of these parameters, it is difficult to obtain consistent results.

Additionally, challenges of ablation catheters include maintaining contact between catheter electrodes and target tissues. For example, a clinician performing an ablation procedure inserts an ablation catheter through a vein in the patient's body, in which the catheter is guided to cardiac tissue in the patient's heart where RF energy is applied through the electrode to the cardiac tissue. Contact between an ablation catheter electrode and cardiac tissue is particularly important in order to ablate the appropriate region of the patient's heart and for efficacy of the treatment for correcting the patient's pathological condition. However, it is difficult to maintain contact between a catheter electrode and a heart wall, such as an endocardial surface of the heart, and prevent the catheter electrode from shifting during an ablation because of the continuous movements of the heart during typical or irregular heartbeat patterns. Clinicians may attempt to apply additional force at a catheter tip to maintain contact between the catheter and the tissue; yet such approaches increase the risk of edema, perforation, and/or bruising of the tissue.

BRIEF SUMMARY

Conventional ablation catheters and methods for providing sufficient ablation treatments are limited because of the challenges associated with maintaining the interaction between catheter electrodes and target tissues during ablation procedures.

In the embodiments presented herein, an ablation catheter with a patterned and textured active area to enhance surface to surface contact between the active area and tissue is described. In some embodiments, the active area of the ablation catheter is an electrode having a patterned and textured surface that increases a coefficient of friction between the target tissue and the electrode during ablation in order to provide proper grip and surface contact. Additionally, the patterned and textured surface of the electrode may improve heat transfer between the electrode of the ablation catheter and the blood surrounding the target tissue. In the embodiments presented herein, devices and methods for performing ablation using ablating catheters with one or more patterned and textured active areas are described.

In an embodiment, an ablation catheter includes a proximal section, a distal section, and a sheath coupled between the distal section and the proximal section. The distal section includes an active area with a patterned, textured surface that is configured to apply RF energy, cryogenic cooling, or laser energy output to a portion of target tissue, such that the portion of target tissue is ablated. The patterned, textured surface of the active area is configured to maintain contact between the target tissue and the active area.

In another embodiment, a catheter for performing tissue ablation in a patient is described. The catheter includes a proximal section, a distal section, and a sheath coupled between the distal section and the proximal section. The distal section includes an active area with a plurality of patterned, textured surfaces, wherein the active area is configured to apply RF energy, cryogenic cooling, or laser energy output to a portion of target tissue, such that the portion of target tissue is ablated. The plurality of patterned, textured surfaces of the active area is configured to maintain contact between the target tissue and the active area.

An example method for performing tissue ablation is described. The method includes providing an ablation catheter for the tissue ablation, wherein the ablation catheter comprises a distal end with one or more active areas, wherein at least one active area comprises a patterned, textured surface. The method further includes ablating a portion of target tissue using RF energy, cryogenic cooling, or laser energy output from the patterned, textured surface of the at least one active area and using the patterned, textured surface of the at least one electrode to facilitate steady contact between the at least one active area and the portion of target tissue.

Further features and advantages, as well as the structure and operation of various embodiments, are described in detail below with reference to the accompanying drawings. It is noted that the specific embodiments described herein are not intended to be limiting. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

Figure 1:
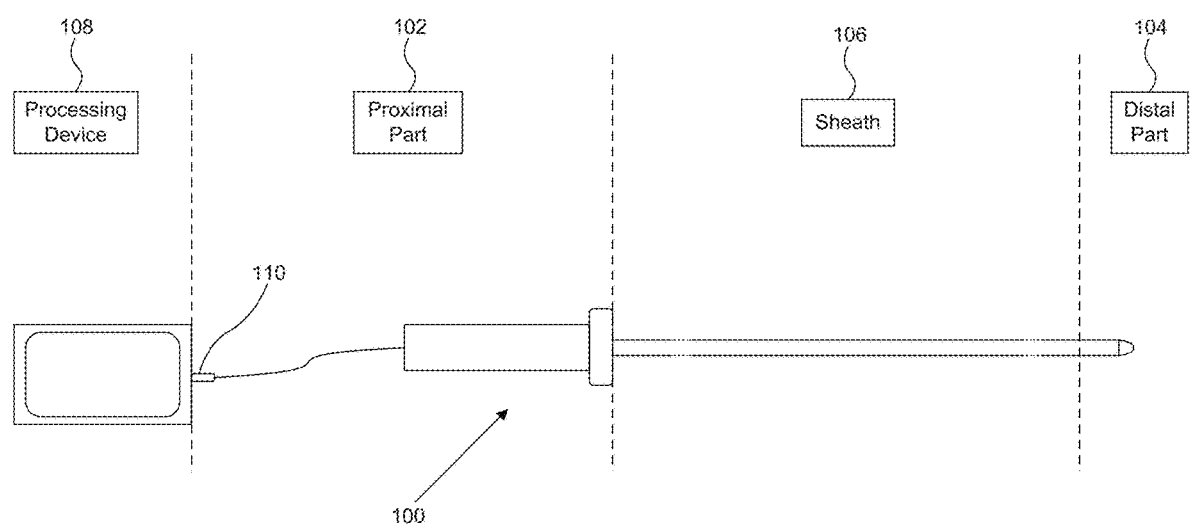
FIG. 1 illustrates an example diagram of a catheter, according to embodiments of the present disclosure.

Embodiments of the present invention will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

It should be noted that although this application may refer specifically to cardiac ablation, the embodiments described herein may target other pathologies as well, along with additional energy sources for ablation. The principles of using RF energy to treat other pathologies are similar, and therefore the techniques used to apply the RF energy are similar.

Disclosed herein are embodiments of an ablation catheter with a patterned, textured active area surface that is configured to enhance device stability and contact between the active area and target tissue during an ablation procedure. As described herein, an active area of an ablation catheter may indicate an electrode that is configured to ablate target tissue. In some embodiments, the patterned, textured surface of the electrode is located at the distal end of an ablation catheter and configured to apply RF energy, laser energy, or cryogenic cooling to a portion of target tissue for tissue ablation. The patterned and textured surface may include a repeating pattern of a predefined shape that is sanded, etched, stamped, machined, or applied by laser ablation to one or more surfaces of the electrode. Each patterned and textured surface of the electrode is electrically conductive and facilitates steady contact between the electrode and target tissue. In particular, the patterned, textured surface of the electrode tip of the ablation catheter has a coefficient of friction value that is higher than the coefficient of friction value of a conventional catheter.

The increased coefficient of friction value of the textured electrode surface enhances device stability of the ablation catheter at the target tissue during ablation procedures for patients and prevents displacement of the electrode from the location of the target tissue. By applying the patterned texture solely to the electrode surface, the distal end of the ablation catheter is stabilized with a proper grip at the patterned, textured surface of the electrode while allowing flexibility to the proximal end and sheath of the ablation catheter to move freely and be directed into specific regions of interest for ablation procedures without obstruction from textures. Although embodiments herein describe the use of an RF ablation catheter, other ablation techniques may be utilized as well without deviating from the scope or spirit of the invention, such as, for example, laser ablation, cryoablation, or the like. Furthermore, the embodiments described herein may be used on any catheter where maintaining contact between one or more active areas at a distal end of the catheter and tissue is desired.

Herein, the terms "electromagnetic radiation," "light," and "beam of radiation" are all used to describe the same electromagnetic signals propagating through the various described elements and systems.

Catheter Embodiments

FIG. 1 illustrates a catheter 100 according to embodiments of the present disclosure. Catheter 100 includes a proximal section 102, a distal section 104, and a sheath 106 coupled between proximal section 102 and distal section 104. In an embodiment, sheath 106 includes one or more radiopaque markers for navigation purposes. In one embodiment, catheter 100 includes a communication interface 110 between catheter 100 and a processing device 108. Communication interface 110 may include one or more wires between processing device 108 and catheter 100. In other examples, communication interface 110 is an interface component that allows wireless communication, such as Bluetooth, WiFi, cellular, etc. Communication interface 110 may communicate with one or more transceiver elements located within either proximal section 102 or distal section 104 of catheter 100.

In an embodiment, sheath 106 and distal section 104 are disposable. As such, proximal section 102 may be reused by attaching a new sheath 106 and proximal section 104 each time a new procedure is to be performed. In another embodiment, proximal section 102 is also disposable. Distal section 104 includes a tip with at least one active area of one or more external, patterned and textured electrodes for ablation, as will be described in further detail below. Each of the one or more electrodes at the tip of the distal section includes at least one surface that is patterned and textured with a predefined, repeating pattern applied to the surface of each electrode by sanding, etching, stamping, electric discharge machining (EDM), casting, laser ablation, or the like. Additionally or alternatively, one or more surfaces of each electrode may be textured with a random pattern by applying a controlled process to the electrode, such as sand-blasting, which results in one or more surfaces with stochastically defined properties such as root mean square (RMS) surface roughness, maximum valley depth, maximum peak height, or average wavelength. The patterned and textured surface of each of the one or more electrodes may include shapes patterned and raised textures to increase surface roughness and friction coefficients at the surface interactions between the electrode(s) and target tissue. For example, the raised textures of a surface may exhibit peak to valley height differences of more than 10 μm. In some embodiments, there may be any number of patterned and textured electrodes at the tip of the distal end of the catheter 100. For simplicity, in the remainder of the description it is considered that only one ablation electrode with one or more patterned and textured surfaces is present at the tip of the catheter. In an embodiment, the tip of the distal section 104 includes a plurality of optical view ports for sending and receiving optical signals. One or more of the optical view ports may be machined in the patterned and textured electrode at the tip of the catheter.

The patterned, textured electrode used for ablation is in electrical connection with at least one cable running along the length of sheath 106. The optical view ports are distributed over the outside of distal section 104, resulting in a plurality of distinct viewing directions, according to an embodiment. In an embodiment, each of the plurality of viewing directions is substantially non-coplanar. The optical view ports may also be designed with irrigation functionality to cool distal section 104 and surrounding tissue from overheating during ablation. Further details on the design of distal section 104 and the patterned, textured electrode of the catheter 100 are discussed with reference to FIGS. 3A, 3B, 4A, and 4B.

Proximal section 102 may house various electrical and optical components used in the operation of catheter 100. For example, a power supply may be included within proximal section 102 to apply RF energy, cryogenic cooling, laser energy, or the like to the patterned, textured electrode located at the tip of distal section 104 for tissue ablation. The power supply may be designed to generate an alternating current at frequencies at least between 350 and 500 kHz. As such, one or more conductive wires (or any electrical transmission medium) may lead from the power supply to distal section 104 within sheath 106. Furthermore, proximal section 102 may include an optical source for generating a beam of radiation. The optical source may include one or more laser diodes or light emitting diodes (LEDs). The beam of radiation generated by the optical source may have a wavelength within the infrared range. In one example, the beam of radiation has a central wavelength of 1.3 μm. The optical source may be designed to output a beam of radiation at only a single wavelength, or it may be a swept source and be designed to output a range of different wavelengths. The generated beam of radiation may be guided towards distal section 104 via an optical transmission medium connected between proximal section 102 and distal section 104 within sheath 106. Some examples of optical transmission media include single mode and multimode optical fibers and integrated optical waveguides. In one embodiment, the electrical transmission medium and the optical transmission medium are provided by the same hybrid medium allowing for both electrical and optical signal propagation.

Proximal section 102 may include further interface elements with which a user of catheter 100 can control the operation of catheter 100. For example, proximal section 102 may include a deflection control mechanism that controls a deflection angle of distal section 104. The deflection control mechanism may require a mechanical movement of an element on proximal section 102, or the deflection control mechanism may use electrical connections to control the movement of distal section 104. Proximal section 102 may include various buttons or switches that allow a user to control when RF energy, cryogenic cooling, laser energy, or the like is applied through the electrode at distal end 104, or when the beams of radiation are transmitted from the electrode at distal end 104, allowing for the acquisition of optical data. In some embodiments, proximal section 102 may include and/or interface with a robotic catheter control system or steering system to steer the catheter 100 to the target tissue.

Figure 2A:
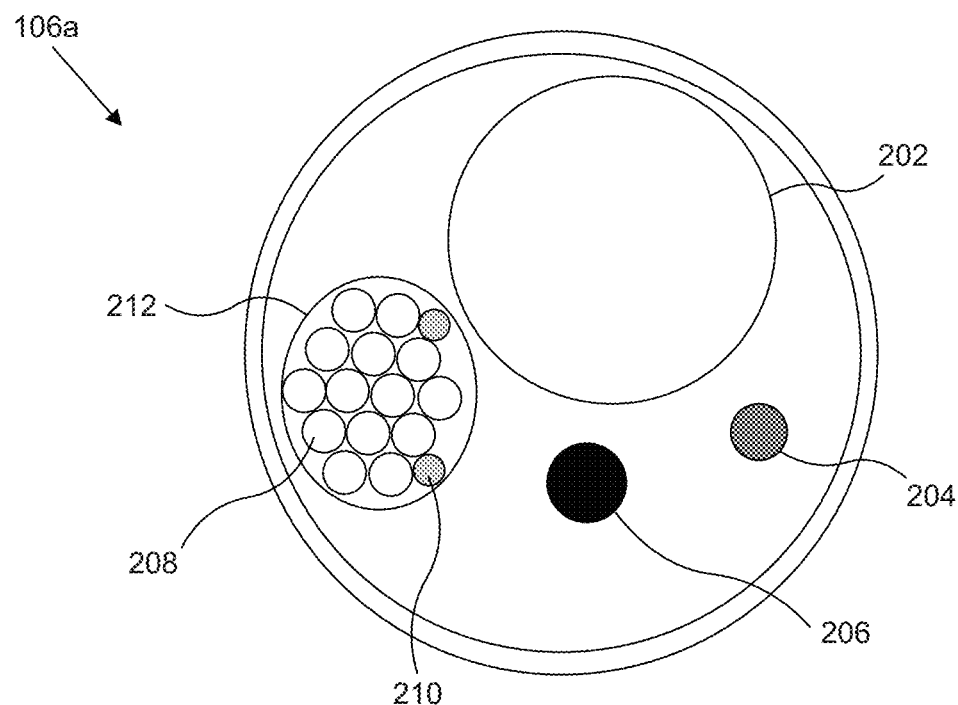
FIGS. 2A and 2B illustrate cross sections of a catheter, according to embodiments of the present disclosure.
Figure 2B:
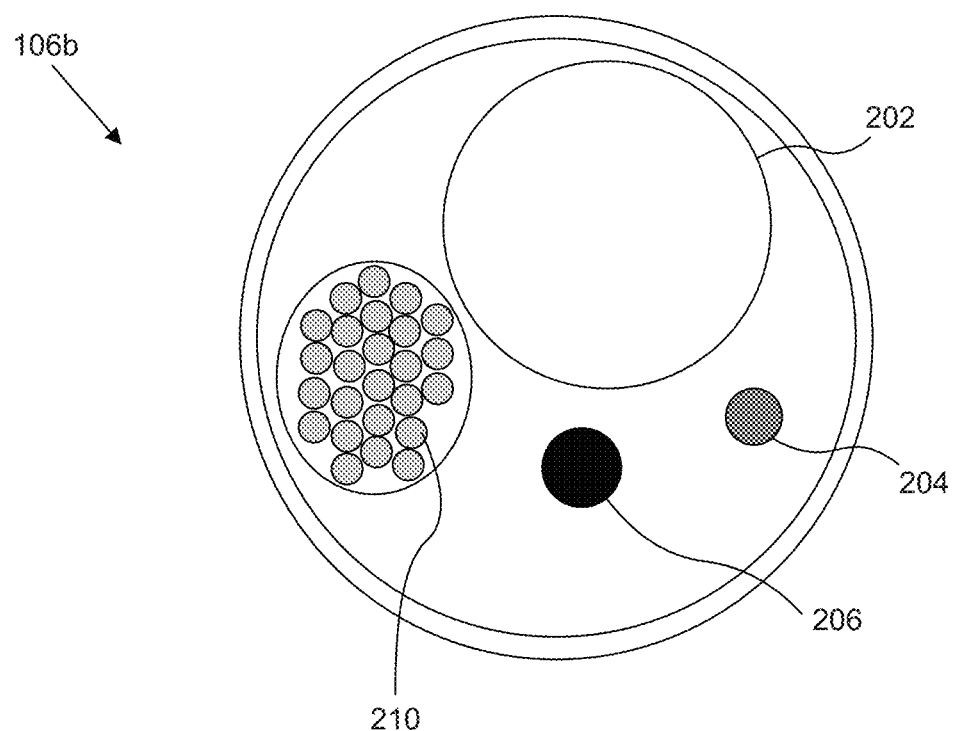

FIGS. 2A and 2B illustrate cross-section views of sheath 106, according to embodiments of the present disclosure. Sheath 106 may include some or all of the elements interconnecting proximal section 102 with distal section 104. Sheath 106a illustrates an embodiment that houses an irrigation channel 202, RF conductive medium 204, deflection mechanism 206, electrical connections 208, and optical transmission medium 210. FIG. 2A illustrates a protective cover 212 wrapped around both electrical connections 208 and optical transmission media 210. Electrical connections 208 may be used to provide signals to optical modulating components located in distal section 104. One or more optical transmission media 210 guide light generated from the optical source (exposure light) towards distal section 104, while another subset of optical transmission media 210 guides light returning from distal section 104 (scattered or reflected light) back to proximal section 102. In another example, the same one or more optical transmission media 210 guides light in both directions.

Irrigation channel 202 may be a hollow tube used to guide cooling fluid towards distal section 104. Irrigation channel 202 may include heating and/or cooling elements disposed along the channel to affect the temperature of the fluid. In another embodiment, irrigation channel 202 may also be used as an avenue for drawing fluid surrounding distal section 104 back towards proximal section 102.

RF conductive medium 204 may be a wire or cable used to provide RF energy to the patterned, textured electrode located at distal section 104. Deflection mechanism 206 may include electrical or mechanical elements designed to provide a signal to distal section 104 in order to change a deflection angle of distal section 104. The deflection system enables guidance of distal section 104 by actuating a mechanical control placed in proximal section 102, according to an embodiment. This system may be based on a series of aligned and uniformly spaced cutouts in sheath 106 aimed at providing unidirectional deflection of distal section 104, in combination with a wire which connects the deflection mechanism control in proximal section 102 with the patterned, textured electrode tip at distal section 104. In this way, a certain movement of the proximal section may be projected to the distal section. Other embodiments involving the combination of several control wires attached to the catheter tip may enable the deflection of the catheter tip along different directions.

FIG. 2B illustrates a cross-section of sheath 106b. Sheath 106b depicts an embodiment having most of the same elements as sheath 106a from FIG. 2A, except that there are no electrical connections 208. Sheath 106b may be used in situations where modulation (e.g., multiplexing) of the generated beam of radiation is performed in proximal section 102.

Patterned and Textured Electrode Embodiments

Figure 3A:
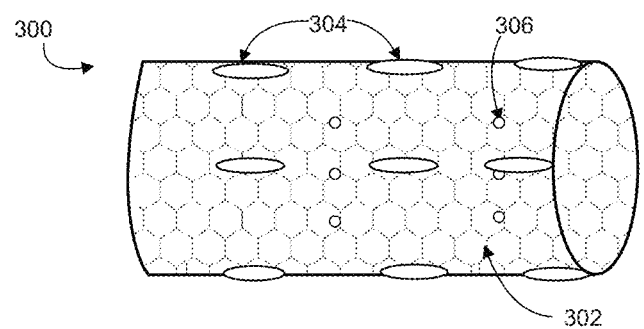
FIGS. 3A and 3B illustrate a patterned, textured electrode located at a distal end of a catheter, according to embodiments of the present disclosure.
Figure 3B:
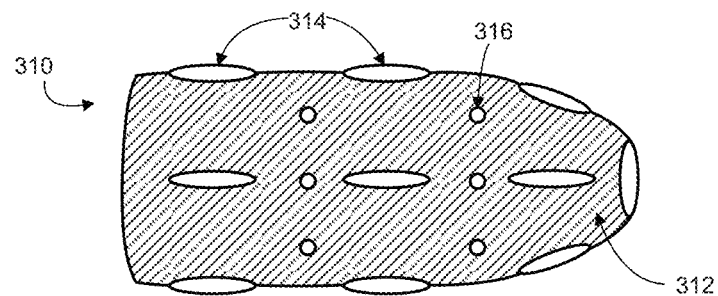

FIGS. 3A and 3B illustrate example diagrams of the patterned, textured electrode located within distal section 104 of catheter 100, according to embodiments of the present disclosure. In particular, FIG. 3A illustrates an example electrode 300. Electrode 300 acts as an outer body of distal section 104, and RF energy, cryogenic cooling, laser energy, or the like is applied to electrode 300 to ablate a portion of target tissue, such as an atrial wall of a patient's heart. Electrode 300 may represent one or more electrodes in distal section 104 and may be referred to herein as one or more active areas. Although the electrode 300 is depicted as a cylindrical shape in FIG. 3A, electrode 300 may be of any shape and/or size for use with the catheter 100 and for ablation of target tissue. For example, electrode 300 may have a diameter in the range of 1.5 mm to 5 mm and a length of 0.1 to 2 cm down from the distal end of the catheter. In some embodiments, electrode 300 may be formed of a material, such as platinum, platinum-iridium alloy, titanium, gold, copper, or another electrically conductive material.

According to an embodiment, electrode 300 includes a patterned texture 302, a plurality of view ports 304, and a plurality of openings 306. Patterned texture 302 may include a predefined, repeating pattern that is applied to one or more surfaces of the electrode 300. Although patterned texture 302 of electrode 300 is shown in FIG. 3A as a hexagonal pattern, the repeating pattern of patterned texture 302 may further include pentagons, octagons, triangles, squares, circles, or other predefined shapes or patterns on the surface of electrode 300. The repeating pattern of patterned texture 302 may have dimensions on the scale of nanometers, micrometers, or millimeters, and patterned texture 302 may be applied to the electrode surface in a direction along the length and/or width of electrode 300. In some embodiments, patterned texture 302 may be applied to all surfaces of electrode 300, as shown in FIG. 3A. In other embodiments, patterned texture 302 may be applied partially on one or more surfaces of electrode 300, such that certain areas of electrode 300 are textured and other areas are left without the texture. Patterned texture 302 may be produced by applying a predefined shape or pattern to one or more surfaces of electrode 300 by laser ablation, electric discharge machining (EDM), casting, stamping, or the like. Additionally or alternatively, patterned texture 302 may be produced by applying a texture to one or more surfaces of electrode 300 by sanding, blasting, etching, or the like.

In some cases, patterned texture 302 may include a random or stochastic design or texture that is applied asymmetrically to the surfaces of electrode 300. Patterned texture 302 may increase surface roughness of electrode 300 and increase a coefficient of friction at the interface between electrode 300 and a target tissue by a factor of three. In some embodiments, patterned texture 302 may result in raised textures, indentations, or grooves in the one or more surfaces of electrode 300 which may prevent electrode 300 from shifting or moving from the target tissue during an ablation procedure. Patterned texture 302 may be designed to facilitate steady contact between the electrode and target tissue such that the target tissue is properly ablated to correct pathological conditions in patients. By applying patterned texture 302 solely to electrode 300 of catheter 100, sheath 106 and proximal section 102 of catheter 100 are flexible and can move (e.g., in blood) without obstructing the catheter from being navigated through the cardiac chamber into the specific tissue or region of interest for the ablation procedure (e.g., tissue of atrial wall). In some embodiments, patterned texture 302 may include a random pattern produced by applying a controlled process, such as sandblasting one or more surfaces of the electrode 300, which results in one or more surfaces with stochastically defined properties such as root mean square (RMS) surface roughness, maximum valley depth, maximum peak height, or average wavelength.

Plurality of view ports 304 may be arranged around the outside of electrode 300 in any pattern to achieve various views of the target tissue. For example, optical fibers (not shown) in distal section 106 may be used at each of plurality of view ports 304 to both transmit and receive light through each of plurality of view ports 304. For example, exposure light is transmitted through view ports 304 away from distal section 103 and onto a portion of target tissue, while light that is scattered or reflected by the portion of target tissue is received through view ports 304. Each view port of plurality of view ports 304 may include more than one optical fiber, for example, a fiber bundle.

Plurality of openings 306 in electrode 300 may be associated with one or more irrigation channels (e.g., irrigation channel 202) located at a tip of the distal end of the catheter. For example, plurality of openings 306 may comprise holes that are used by the irrigation channels to deliver fluid to tissue for cooling during the ablation procedure. In other embodiments, plurality of openings 306 may be designed to deliver therapeutic fluids to a sample or target tissue.

FIG. 3B illustrates another embodiment of the patterned, textured electrode, depicted as electrode 310. In some embodiments, electrode 310 may be similar to electrode 300 depicted in FIG. 3A. Electrode 310 is depicted as a different shape than electrode 300 by way of example. Electrode 310 further includes a patterned texture 312, a plurality of view ports 314, and a plurality of openings 316. In some embodiments, patterned texture 312, plurality of view ports 314, and plurality of openings 316 may be the same as or similar to patterned texture 302, plurality of view ports 304, and plurality of openings 306, respectively, of electrode 300 depicted in FIG. 3A. In particular, patterned texture 312 shown in FIG. 3B includes a repeating diagonal line pattern along the length of electrode 310. By selecting different patterns for the electrode, the resulting patterned, textured electrode may be customized with a particular coefficient of friction value based on the type of patterned texture applied to the electrode of catheter 100.

Figure 4A:
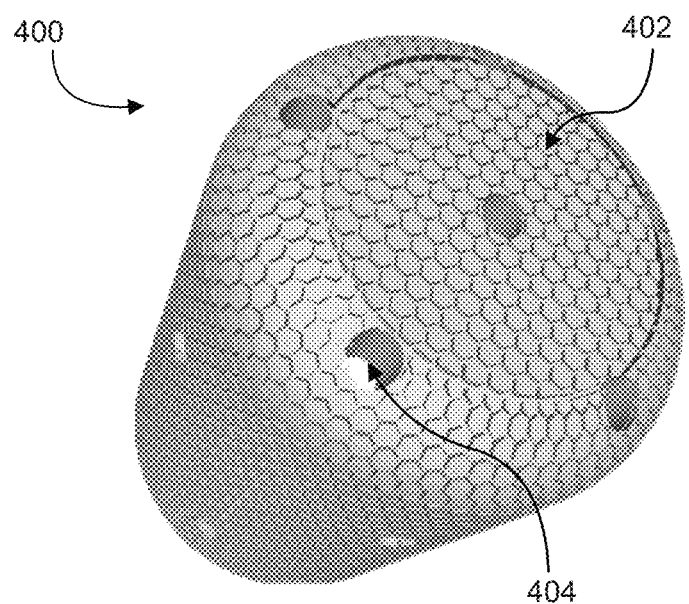
FIGS. 4A and 4B illustrate example diagrams of patterned, textured electrode surfaces, according to embodiments of the present disclosure.
Figure 4B:
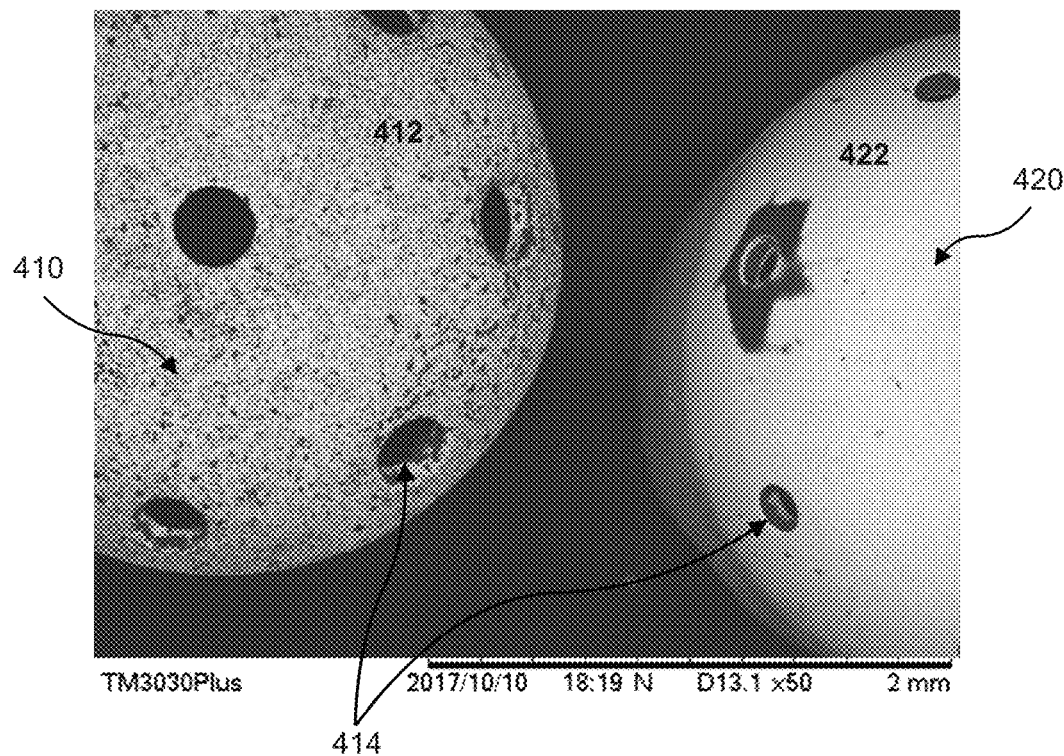

FIGS. 4A and 4B illustrate example diagrams of patterned, textured electrode surfaces, according to embodiments of the present disclosure. FIG. 4A illustrates electrode 400 of an ablation catheter, including a patterned texture 402 and a plurality of view ports 404. Patterned texture 402 may include a repeating hexagonal pattern that is applied to one or more surfaces of electrode 400, resulting in raised hexagonal structures that protrude from the surfaces of electrode 400. In another example, the hexagons of patterned texture 402 may be machined into one or more surfaces of electrode 400, resulting in indentations or recesses on the surface(s) of electrode 400. Additionally, plurality of view ports 404 may be arranged around the outside of electrode 400 in any pattern to achieve various views of the target tissue during an ablation procedure.

FIG. 4B illustrates an additional example of patterned, textured electrode 410. Electrode 410 includes a patterned texture 412 with a plurality of view ports 414. Patterned texture 412 may be a random design or texture that is applied asymmetrically to a surface of electrode 410. For example, patterned texture 412 may be produced by sanding or abrasion blasting to roughen the electrode surface and increase a coefficient of friction of the electrode surface.

FIG. 4B further illustrates electrode 420, which includes a surface 422 and a plurality of view ports 414. Surface 422 of electrode 420 may be polished or smooth without any patterned texture applied to surface 422. In some embodiments, electrode 410 may have a higher coefficient of friction value than a coefficient of friction value of electrode 420.

Figure 5:
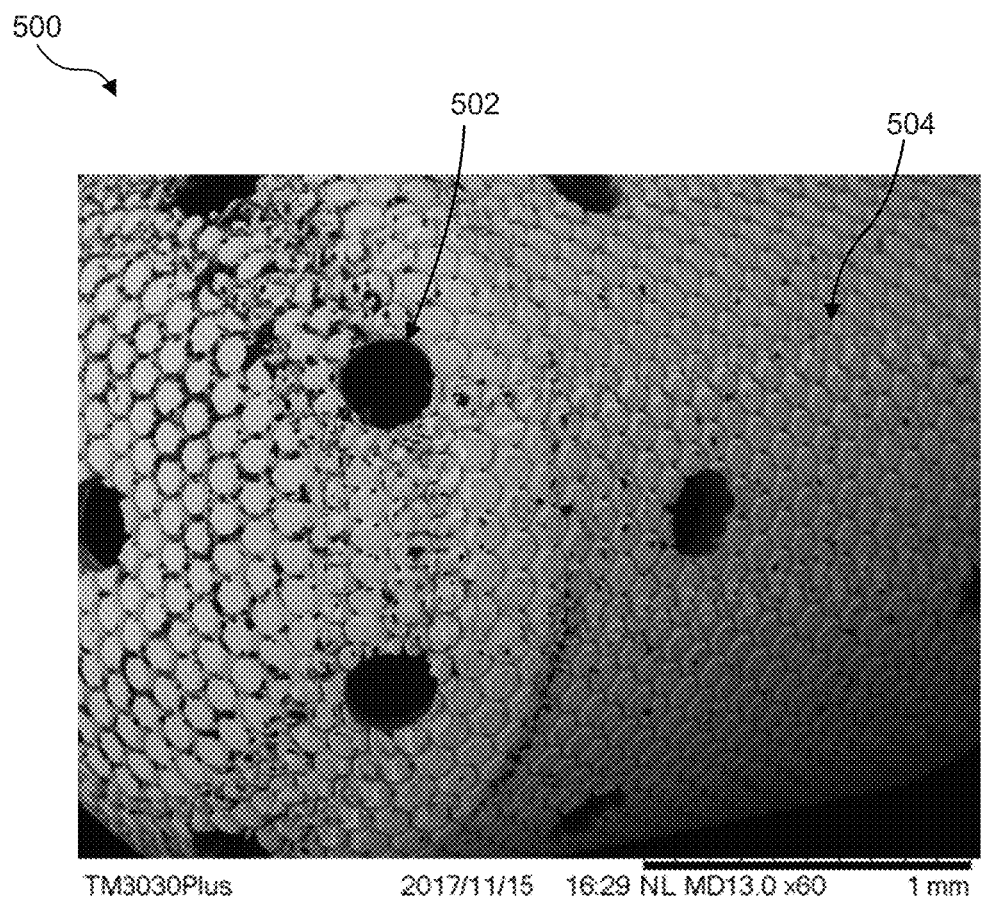
FIG. 5 illustrates an example image of a patterned, textured electrode, according to embodiments of the present disclosure.

FIG. 5 illustrates an example image of a patterned, textured electrode, according to embodiments of the present disclosure. In particular, FIG. 5 illustrates a scanning electron microscopy (SEM) image of a patterned, textured electrode 500 of an ablation catheter. The patterned, textured electrode 500 includes a patterned texture 502 and a plurality of view ports 504. Patterned texture 502 may be a repeating hexagonal pattern that is applied to a plurality of surfaces of the electrode 500 by laser ablation. Additionally, the plurality of view ports 504 may be arranged around the outside of the patterned, textured electrode 400 in any pattern to achieve various views of the target tissue during an ablation procedure.

Figure 6:
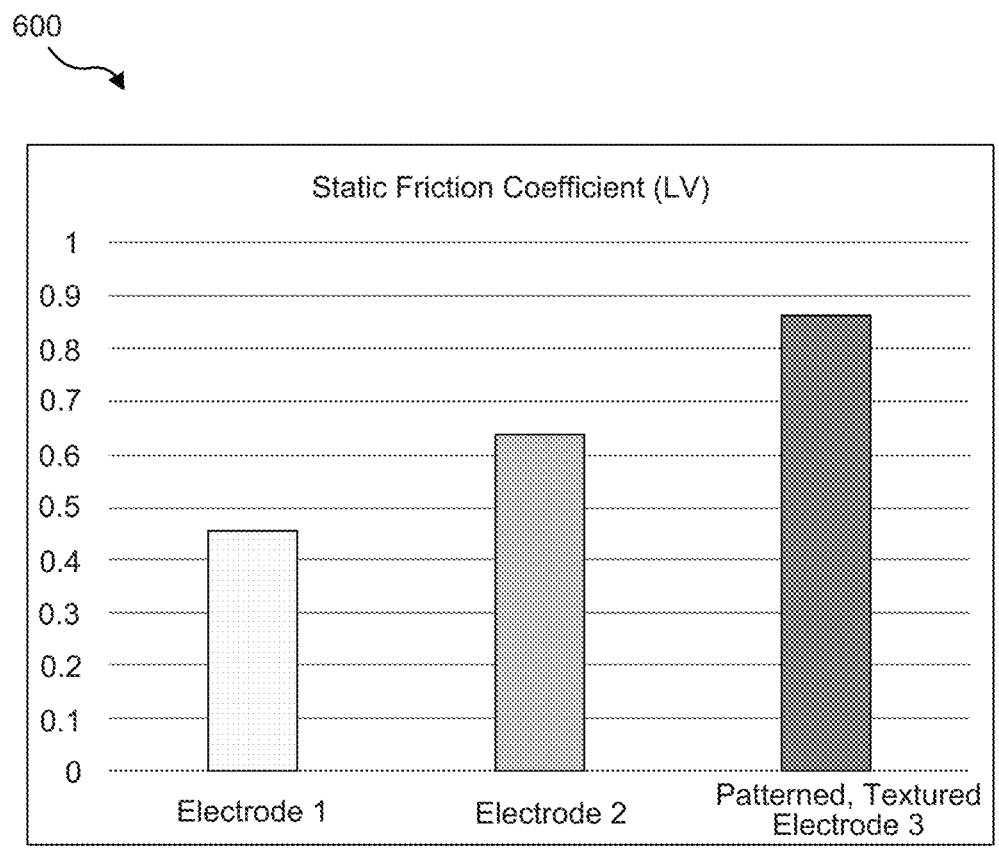
FIG. 6 illustrates an example graph of friction coefficient values for various ablation catheter electrodes, according to embodiments of the present disclosure.

FIG. 6 illustrates an example graph 600 of friction coefficient values for various ablation catheter electrodes, according to embodiments of the present disclosure. For example, graph 600 provides values of static friction coefficients for "Electrode 1," "Electrode 2," and "Patterned, Textured Electrode 3." In some embodiments, the static friction coefficient value for each electrode may be measured at the interface between the electrode and ventricular tissue. "Electrode 1" and "Electrode 2" may represent polished and/or smooth ablation catheter electrodes without any patterned texture applied to one or more electrode surfaces. "Patterned, Textured Electrode 3" may represent a patterned, textured ablation catheter electrode, in which a patterned texture has been applied to one or more surfaces of the electrode, as described herein. As shown in FIG. 6, applying a patterned texture to one or more surfaces of an ablation catheter electrode results in an increased static friction coefficient value with respect to the static friction coefficient values of ablation catheter electrodes without any patterned texture.

Example Method of Operation

Catheter 100 may be used to perform ablation by applying high-frequency alternating current to tissue in contact with the patterned, textured electrode of distal section 104 of catheter 100. Oscillating frequencies ranging from 350 to 500 kHz may be used. It should be understood that other frequencies may be used as well and that any frequencies above about 1 kHz rarely produce electrical stimulation of excitable cells. An adjustable-power high-frequency power source providing the RF energy to electrode 306 at distal section 104 may be used. The physics underlying the heat transfer to tissue is based on a high electrical impedance of the patterned, textured electrode-tissue interface. The impedance of this tissue-electrode interface, at the ablation frequency, may be substantially greater than that of the returning electrode. For a given current delivered though the body, a greater voltage drop may be generated at this interface producing heat at the desired location. In this way, a small tissue volume surrounding the patterned, textured electrode is ablated, instead of all the tissue volume from the patterned, textured electrode of the catheter to the ground contact, which is typically placed on the patient's back during cardiac ablation treatment. By adjusting the RF power and ablation time, the total energy delivered to tissue may be accurately controlled. Other ablation techniques based on cryogenic or optical means (e.g., laser ablation) may also be used for the treatment of different pathologies. In additional embodiments, the patterned, textured electrode-tissue interface may also provide additional cooling to surrounding blood flow around the target tissue. This benefit may be achieved through the turbulence promoting effect of texture, which may result in an increased Nusselt number and improved heat transfer to the surrounding fluid around the target tissue.

Various ablation methods and other embodiments of ablation catheters with patterned, textured electrodes described thus far can be implemented, for example, using catheter 100 shown in FIG. 1, along with one or more patterned, textured electrodes, such as electrodes 300, 310, 400, 410, or 500 shown in FIGS. 3A, 3B, 4A, 4B, and 5, respectively.

Figure 7:
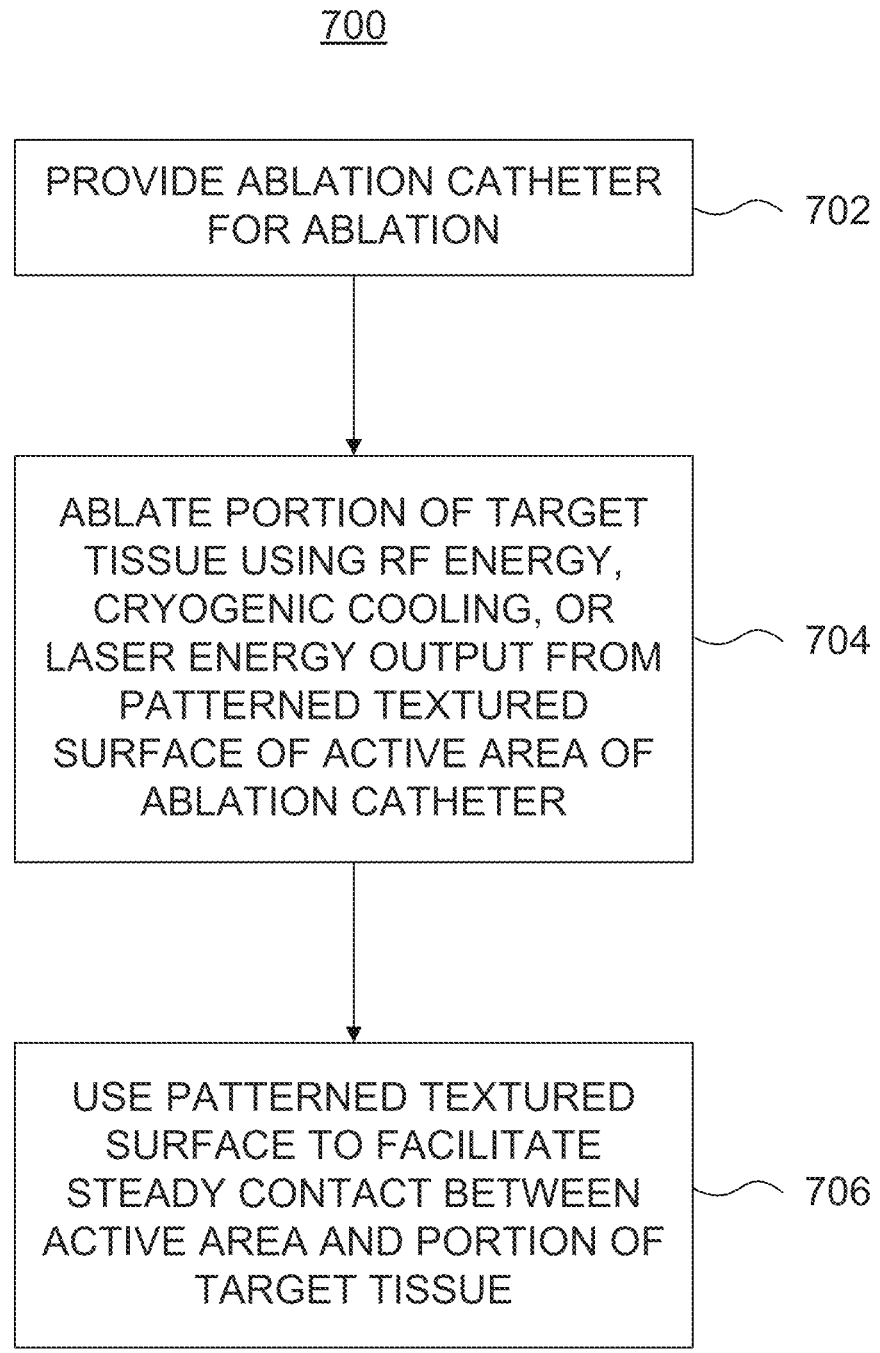
FIG. 7 illustrates an example method, according to embodiments of the present disclosure.

FIG. 7 illustrates an example method 700 for performing ablation according to embodiments of the present disclosure. Method 700 may be performed by ablation catheters with one or more patterned textured electrodes as described herein (e.g., electrodes 300, 310, 400, 410, and/or 500).

At block 702, an ablation catheter for ablation is provided. For example, an ablation catheter with one or more active areas at the distal end of the ablation catheter is provided, in which at least one active area includes a patterned, textured surface. For example, the at least one active area may include at least one electrode, in which the patterned, textured surface of the at least one electrode may be produced by applying a predefined pattern to a surface of the at least one electrode by laser ablation, electric discharge machining (EDM), sanding, blasting, etching, casting, or stamping.

At block 704, a portion of target tissue is ablated using RF energy, cryogenic cooling, or laser energy output from the patterned, textured surface of the at least one active area of the ablation catheter. For example, the patterned, textured surface may be electrically conductive, and RF energy, cryogenic cooling, or laser energy may be output to ablate a portion of target tissue, such as a portion of one or more layers of an atrial wall in a patient's heart.

At block 706, the patterned, textured surface of the at least one active area may be used to facilitate steady contact between the at least one active area and the portion of target tissue. For example, the patterned, textured surface may increase a friction coefficient of contact between the target tissue and the at least one electrode and prevent one or more active areas of the catheter from shifting or moving from the target tissue during an ablation procedure.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An ablation catheter comprising:
a proximal section;
a distal section comprising:
an active area, wherein a surface of the active area comprises a patterned texture and is configured to apply radiofrequency (RF) energy, cryogenic cooling, or laser energy output to a portion of a target tissue, such that the portion of the target tissue is ablated; and
a plurality of view ports surrounded by the patterned texture, the plurality of view ports being configured to send and receive optical signals to and from the target tissue; and
a sheath coupled between the proximal section and the distal section, wherein the patterned texture is configured to increase a friction coefficient of contact between the target tissue and the active area, maintain contact between the target tissue and the active area, and prevent movement of the target tissue relative to the active area during a time of an ablation procedure.

2. The ablation catheter of claim 1, wherein:
the active area is an electrode comprising at least one of platinum, platinum-iridium alloy, titanium, gold, or copper, the electrode comprises a diameter in a range of about 1.5 mm to 5 mm and a length in a range of about 0.1 cm to 2 cm, and the patterned texture is electrically conductive.

3. The ablation catheter of claim 2, wherein the patterned texture comprises a repeating pattern throughout a body of the electrode.

4. The ablation catheter of claim 2, wherein the patterned texture comprises a hexagonal pattern along the length of the electrode.

5. A method for performing tissue ablation, the method comprising:
providing an ablation catheter for the tissue ablation, wherein the ablation catheter comprises a distal end with one or more active areas, wherein at least one active area comprises a patterned, textured surface and a plurality of view ports surrounded by the patterned, textured surface;
ablating a portion of a target tissue using radiofrequency (RF) energy, cryogenic cooling, or laser energy output from the patterned, textured surface of the at least one active area;
using the patterned, textured surface to increase a friction coefficient of contact between the portion of the target tissue and the at least one active area, facilitate steady contact between the at least one active area and the portion of the target tissue, and prevent movement of the target tissue relative to the at least one active area; and
using the plurality of view ports arranged on the patterned, textured surface to send and receive optical signals to and from the target tissue.

6. The method of claim 5, wherein:
the one or more active areas comprise one or more electrodes comprising at least one of platinum, platinum-iridium alloy, titanium, gold, or copper, the one or more electrodes each comprise a diameter in a range of about 1.5 mm to 5 mm and a length in a range of about 0.1 cm to 2 cm, and the patterned, textured surface of each electrode is electrically conductive.

7. The method of claim 6, wherein the patterned, textured surface of the one or more electrodes comprises a repeating pattern throughout a body of each electrode.

8. The method of claim 6, further comprising:
producing the patterned, textured surface of the one or more electrodes of the ablation catheter.

9. The method of claim 8, wherein producing the patterned, textured surface further comprises:
applying a predefined pattern to a surface of the one or more electrodes by laser ablation, resulting in the patterned, textured surface of the one or more electrodes.

10. The method of claim 8, wherein producing the patterned, textured surface further comprises:
applying a predefined pattern to a surface of the one or more electrodes by electric discharge machining (EDM), resulting in the patterned, textured surface of the one or more electrodes.

11. The method of claim 8, wherein producing the patterned, textured surface further comprises:
applying a texture to a surface of the one or more electrodes by sanding, blasting, etching, casting, or stamping the surface of each electrode, resulting in stochastically defined surface properties of each electrode.

12. A catheter for performing tissue ablation in a patient, the catheter comprising:
a proximal section;
a distal section comprising:
an active area comprising a plurality of patterned, textured surfaces, wherein the active area is configured to apply radiofrequency (RF) energy, cryogenic cooling, or laser energy output to a portion of a target tissue, such that the portion of the target tissue is ablated, wherein the active area further comprises a plurality of view ports surrounded by the plurality of patterned, textured surfaces, the plurality of view ports being configured to send and receive optical signals to and from the target tissue; and
a sheath coupled between the proximal section and the distal section, wherein the plurality of patterned, textured surfaces of the active area is configured to increase a friction coefficient of contact between the target tissue and the active area, maintain contact between the target tissue and the active area, and prevent movement of the target tissue relative to the active area during a time of an ablation procedure.

13. The catheter of claim 12, wherein:
the active area is an electrode comprising at least one of platinum, platinum-iridium alloy, titanium, gold, or copper, the electrode comprises a diameter in a range of about 1.5 mm to 5 mm and a length in a range of about 0.1 cm to 2 cm, and the plurality of patterned, textured surfaces of the electrode is electrically conductive.

14. The catheter of claim 12, wherein the proximal section interfaces with a robotic catheter control system.

15. The catheter of claim 13, wherein each patterned, textured surface of the electrode improves heat transfer between the electrode and blood surrounding the target tissue.

16. The ablation catheter of claim 1, wherein the patterned texture comprises raised textures with peak to valley height differences greater than about 10 microns.

17. The ablation catheter of claim 1, wherein the active area comprises an electrode having a tubular body that forms a catheter tip of the distal section, and wherein the patterned texture is arranged on an entirety of the tubular body at the catheter tip.

18. The ablation catheter of claim 1, wherein each view port of the plurality of view ports comprises an optical fiber.

19. The ablation catheter of claim 1, wherein the distal section further comprises a plurality of openings configured to deliver a fluid to the portion of the target tissue, wherein each of the plurality of openings is surrounded by the patterned texture.

20. The method of claim 5, further comprising providing a fluid to the portion of the target tissue through a plurality of openings through the patterned, textured surface.

\* \* \* \* \*